United States Patent [19]

Nishiguchi

[11] Patent Number: 5,583,270

[45] Date of Patent: *Dec. 10, 1996

[54] PROCESS FOR THE PREPARATION OF 1,3-BUTYLENE GLYCOL

[75] Inventor: Kazuhisa Nishiguchi, Ohtake, Japan

[73] Assignee: Daicel Chemical Industries, Ltd., Osaka-fu, Japan

[*] Notice: The term of this patent shall not extend beyond the expiration date of Pat. No. 5,345,004.

[21] Appl. No.: 264,733

[22] Filed: Jun. 23, 1994

Related U.S. Application Data

[63] Continuation-in-part of Ser. No. 163,308, Dec. 8, 1993, Pat. No. 5,345,004.

[30] Foreign Application Priority Data

| Mar. 24, 1993 | [JP] | Japan | 4-65186 |
| Jun. 24, 1993 | [JP] | Japan | 4-1153856 |
| Nov. 1, 1993 | [JP] | Japan | 4-273829 |

[51] Int. Cl.$^6$ ............................................. C07C 29/141

[52] U.S. Cl. ..................... 568/865; 568/853; 568/858; 568/862; 568/881

[58] Field of Search .......................... 568/862, 881, 568/858, 853, 865

[56] References Cited

U.S. PATENT DOCUMENTS

| 4,608,446 | 8/1986 | Möhzing et al. | 568/863 |
| 5,345,004 | 9/1994 | Nishiguchi | 568/865 |

OTHER PUBLICATIONS

Smeykal et al.; Chem. Abs. 69:86255w (1968).

Primary Examiner—Gary Geist
Attorney, Agent, or Firm—Morgan & Finnegan, L.L.P.

[57] ABSTRACT

Disclosed are the improvements of a process for the preparation of 1,3-butylene glycol, in which the generation of by-products can be decreased, resulting in being capable of productiong 1,3-butylene glycol having high quality (e.g. an odorless, so-called "cosmetic grade") at a high-yield.

19 Claims, 4 Drawing Sheets

PROCESS FOR THE PREPARATION OF 1,3-BUTYLENE GLYCOL

This application is a continuation-in-part of U.S. Ser. No. 08/163.308, filed on Dec. 8. 1993 now U.S. Pat. No. 5,345,004.

FIELD OF THE INVENTION

The present invention relates to an improved process for the preparation of 1,3-butylene glycol.

In particular, the present invention relates to the improvements of a process for the preparation of 1,3-butylene glycol, in which the generation of by-products can be decreased, resulting in it being capable of obtaining 1,3-butylene glycol having high quality (e.g. odorless) at a high yield.

BACKGROUND OF THE INVENTION 1,3-butylene glycol is an organic compound which has a boiling point of 208° C. under ordinary pressure, is viscous, colorless, transparent and low odor, exhibits an excellent solubility and a capability of producing chemically-stable derivatives, and is a useful compound as a solvent for coatings, starting materials for various synthetic resins and surfactants, a high-boiling-point solvent and antifreeze, food supplements, animal food supplements, a humectant for tobacco composition and an intermediate for preparation of various other compounds.

Recently in particular, high-quality odorless 1,3-butylene glycol has been used as a solvent for toiletry products in the field of cosmetics due to its excellent moisture absorptive property, low volatility, low irritation and low toxicity.

However, the scope for the application of 1,3-butylene glycol is limited due to a very minor quantity of residual odor.

Most recently in particular, further improvement in the quality and the yield of an odorless, so-called "cosmetic grade" 1,3-butylene glycol has been strongly desired.

Heretofore, there have been three widely-known processes for the preparation of 1,3-butylene glycol which are described below.

(1) A method (British Patent N° 853266) in which acetaldol is first prepared by aldol condensation of acetaldehyde, and then catalytically hydrogenated to obtain 1,3-butylene glycol.

(2) A method in which 1,3-butylene glycol is prepared by a hydration reaction of 1,3-butyleneoxide.

(3) A method in which 1,3-butylene glycol is prepared from propylene and formaldehyde by the Prince Reaction.

However, method (2) is not yet completed for use as an industrial manufacturing process, and therefore is unpractical.

And, method (3) is also unpractical because it gives only a low yield.

Therefore, 1,3-butylene glycol has been industrially manufactured by method (1).

However, acetaldol is not stable due to its chemical structure.

For example, croton aldehyde is produced by dehydration of acetaldol, resulting in the production of various impure materials as by-products, for example, butanol, 2-butanone, etc.

It is known that the above-mentioned acetaldol produced industrially is primarily composed of 2,4-dimethyl-1,3-dioxane-6-ol(aldoxane) which is a trimer of acetaldehyde as described in Industrial Engineering Chemistry 44, 1003 (1952).

It is self-evident that if aldoxane is catalytically reduced, it would be decomposed by hydrogenation into 1,3-butylene glycol and ethanol as a reaction mechanism, which makes it objectionable for the purpose of industrially manufacturing 1,3-butylene glycol.

As a method for solving the problem, for example, Japanese Patent Unexamined Publications 212384/1987 and 246529/1987 disclose that a crude reaction solution primarily consisting of paraldol is prepared while distilling out acetaldehyde after thermally decomposing aldoxane, followed by catalytically reducing paraldol to prepare 1,3-butylene glycol.

Heretofore, unreacted acetaldehyde [a primary component in stream (C) of FIG. 1] distilled out in a step [aldoxane decomposing column 1–3 in FIG. 1] for preparing a solution [stream (B) of FIG. 1] primarily consisting of aldoxane and paraldol in which aldoxane [a primary component in stream (A) of FIG. 1] is thermally decomposed, has been recirculated [stream line (F)] to the aldol condensation step (a) [1-1 of FIG. 1].

In such an acetaldehyde-recirculating method, croton aldehyde generated in the thermal decomposition step (b) [1-3 of FIG. 1] of aldoxane is also recirculated to the aldol condensation step together with unreacted acetaldehyde, unpreferably resulting in the generation of various impure components by a reaction with acetaldehyde, etc. in the aldot condensation step.

The impure components, in particular, odor-causing impurities cannot be sufficiently removed in succeeding steps [e.g. ethanol/butanol distillation columns, water distillation column, etc.], resulting in it adversely affecting to the quality (e.g. odor regulation) of 1,3-butylene glycol products for their uses in the field of cosmetics.

Almost all of the water is removed together with the unreacted acetaldehyde through the thermal decomposition step of aldoxane and the simultaneous acetaldehyde distillation as described above, objectionably resulting in it becoming unsuitable of practical operation due to viscosity increase or crystallization of the crude solution discharged from the bottom of the decomposition column.

Furthermore, conventional 1,3-butylene glycol products prepared by the hydrogenation of paraldol after removing croton aldehyde as described above include minor amounts of odor-causing impurities even after being refined through the conventional refining steps described below.

The conventional refining steps primarily have included an ethanol distillation step, a butanol distillation step, a water distillation step, a salts-removing step, a step for removing high-boiling-point ingredients and a step for removing low-boiling-point ingredients, leading to the production of a refined 1,3-butylene glycol.

On the other hand, it is known (e.g. Japanese Examined Patent Publication N° 80139/1991) that very minor amounts of odor-causing impurities can be acceleratedly removed by distillation while charging water so as to obtain an odorless 1,3-butylene glycol (e.g. a product having a purity of 99.7–99.97%) from a 1,3-butylene glycol product having odor (e.g. a commercially supplied product having a purity of more than 98%).

Even though the method described in the Publication n° 80139/1991 is carried out, the odorless 1,3-butylene glycol an be obtained only at a yield of 50 to 60%.

The present invention has been completed as a result of studies by the present inventor to solve the above-described problems.

SUMMARY OF THE INVENTION

An object of the present invention is to provide a process for the preparation of 1,3-butylene glycol having a high quality and at a high yield.

A first aspect of the present invention is an improved process for the preparation of 1,3-butylene glycol by steps (a), (b) and (c);
(a) aldol condensation of acetaldehyde in the presence of an alkali catalyst to obtain a reaction crude solution primarily containing aldoxane, acetaldehyde and water;
(b) thermal decomposition of aldoxane to obtain paraldol while distilling off a distillate containing acetaldehyde, water and small amounts of croton aldehyde from the reaction crude solution;
(c) hydrogenation of paraldol to obtain 1,3-butylene glycol in the presence of a catalyst;
characterized in that a refined acetaldehyde not containing a substantial amount of croton aldehyde is recirculated to step (a) after removal of croton aldehyde from the distillate in step (b).

According to a specific advantageous embodiment, said removal of croton aldehyde is carried out in an acetaldehyde distillation column having a side-stream recirculating line equipped with a decanter.

A second aspect of the present invention is an improved process for the preparation of 1,3-butylene glycol by steps (a), (b) and (c) described hereinabove; characterized in that water is charged into the aldoxane decomposition column in step (b).

According to an advantageous embodiment, said water is water discharged from the bottom of an acetaldehyde distillation column.

A third aspect of the present invention is an improved process for the preparation of 1,3-butylene glycol by steps (a), (b) and (c) described hereinabove; characterized in that fresh water is charged into the top of a distillation column while removing water after having removed ethanol and butanol from a crude 1,3-butylene glycol solution containing ethanol and butanol generated in said hydrogenation step (c).

According to an advantageous embodiment, said fresh water is deionized water.

Step (a) includes an aldol condensation reactor (1-1), and also as a supplement includes a neutralization tank (1-2). Step (b) includes an aldoxane decomposition column (1-3), and supplementarily includes an acetaldehyde-refining column (1-4).

Figure 2:
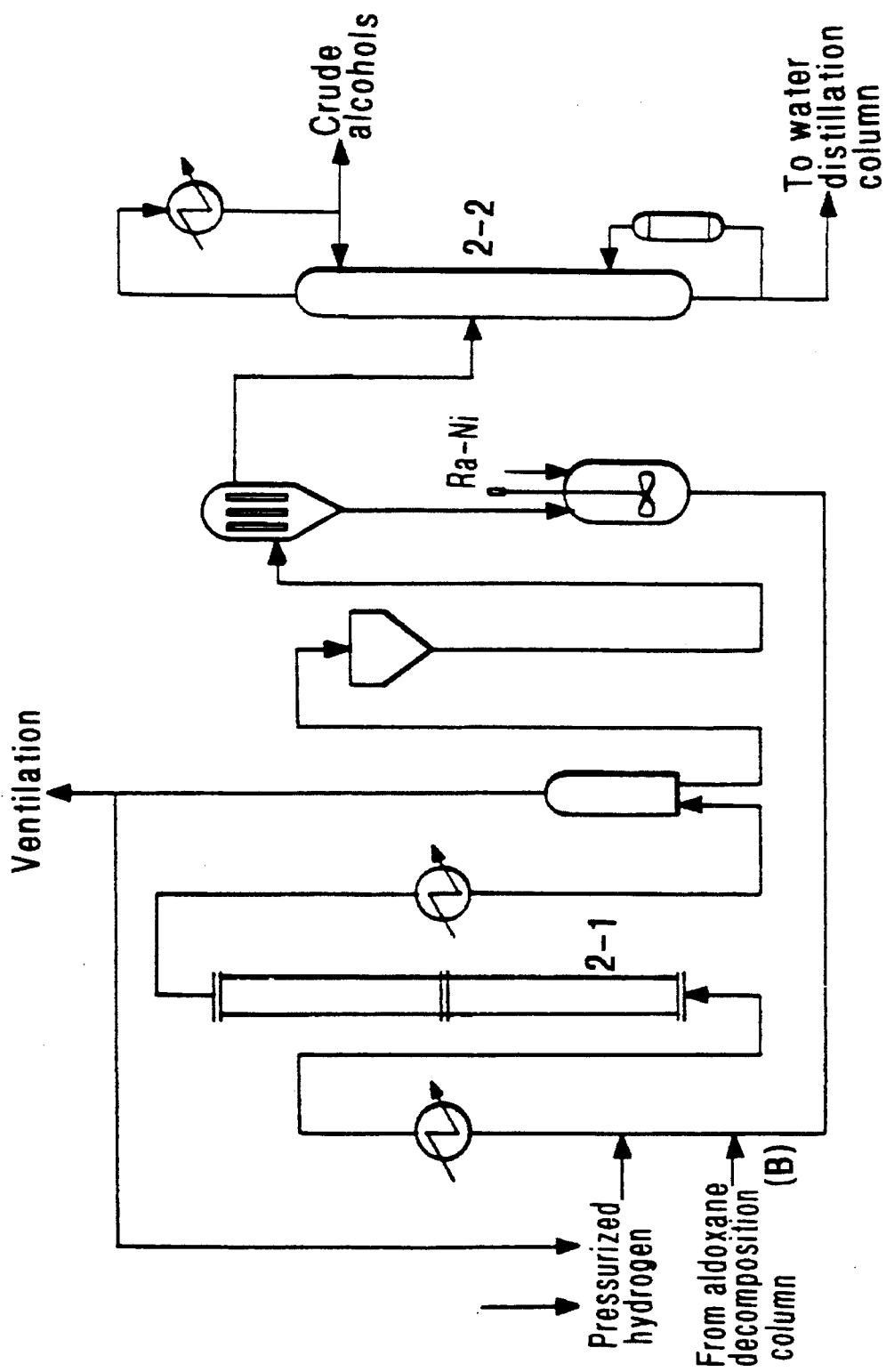

FIG. 2 is a block diagram exhibiting a process for preparing 1,3-butylene glycol in which step (c) is shown.

Step (c) includes a hydrogenation reactor (2-1) and alcohols distillation column (2-2).

Figure 3:
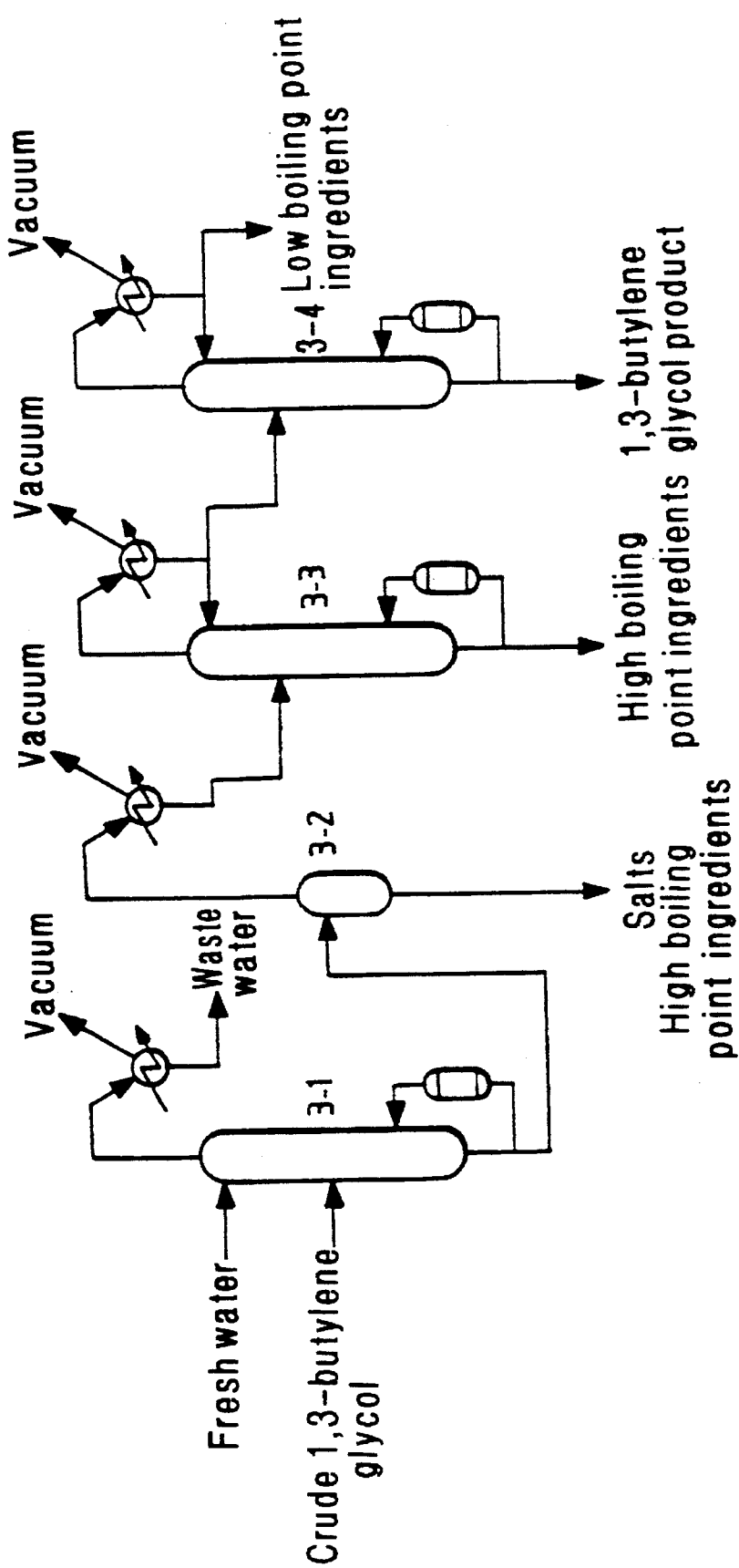

FIG. 3 is a block diagram exhibiting a step for refining a crude 1,3-butylene glycol, in which a water-distillation column (3-1), a salts-removing column (3-2) and a distillation column (3-3) for removing high-boiling-point ingredients and a distillation column (3-4) for removing low-boiling-point ingredients.

Figure 4:
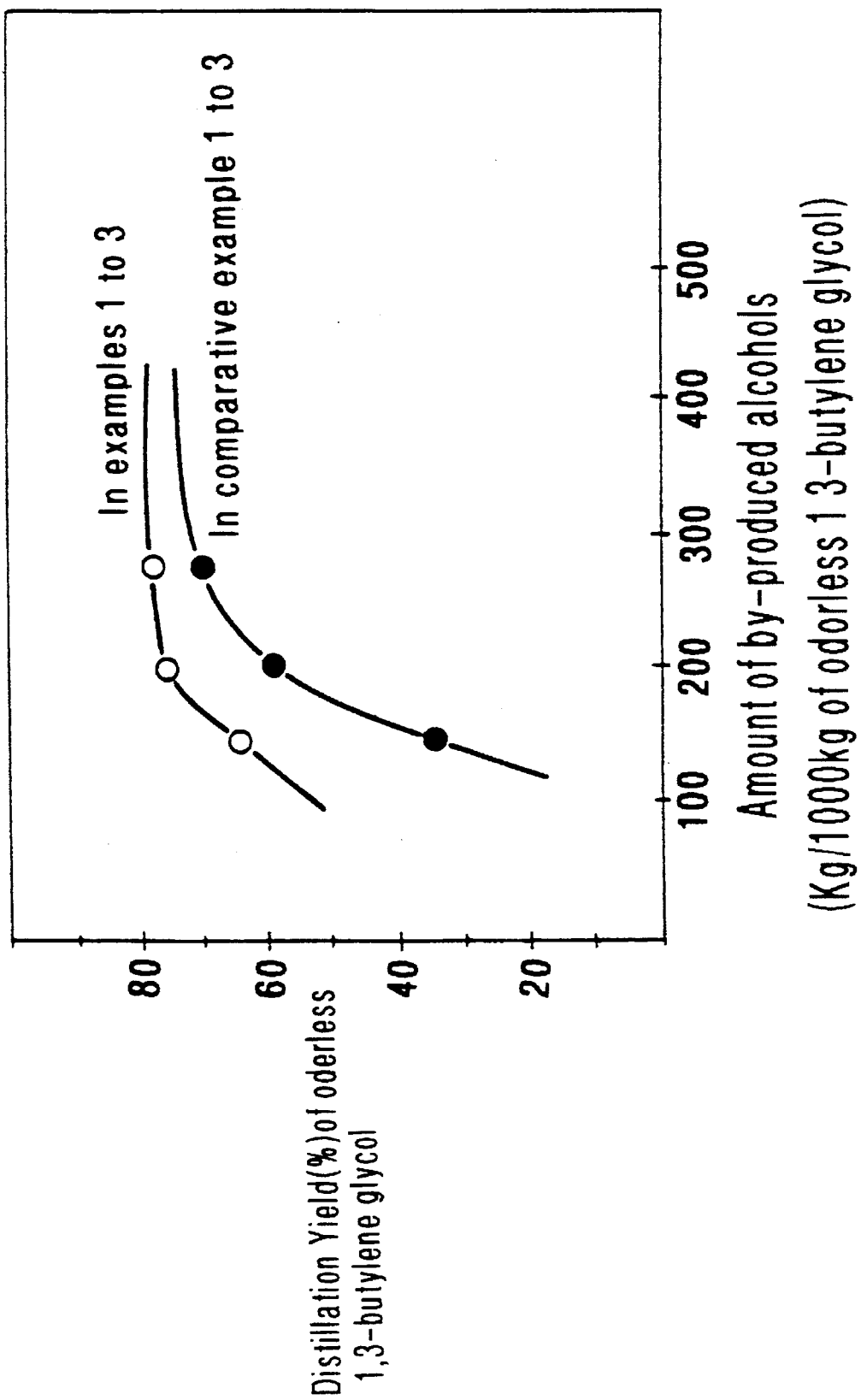

FIG. 4 is a graph in which the distillation yield of odorless 1,3-butylene glycol products is shown in the ordinate, and the amount of by-produced alcohols based on 1000 of odorless 1,3-butylene glycol products is shown in the abscissa.

DETAILED DESCRIPTION OF THE INVENTION

The present invention is described hereinafter in more detail based on accompanying FIGS. 1 to 3 which are a block diagram exhibiting a process for preparing 1,3-butylene glycol in which steps (a), (b) and (c) are combinedly shown.

In accordance with a first aspect of the present invention, there is provided an improved process for the preparation of 1,3-butylene glycol by steps (a), (b) and
(a) aldol condensation of acetaldehyde in the presence of an alkali catalyst to obtain a crude reaction solution primarily containing aldoxane, acetaldehyde and water;
(b) thermal decomposition of aldoxane to obtain paraldol while distilling off a distillate containing acetaldehyde, water and small amounts of croton aldehyde from the crude reaction solution;
(c) hydrogenation of paraldol to obtain 1,3-butylene glycol in the presence of a catalyst;
characterized in that a refined acetaldehyde not containing a substantial amount of croton aldehyde is recirculated to step (a) after the removal of croton aldehyde from the distillate in step (b).

Figure 1:
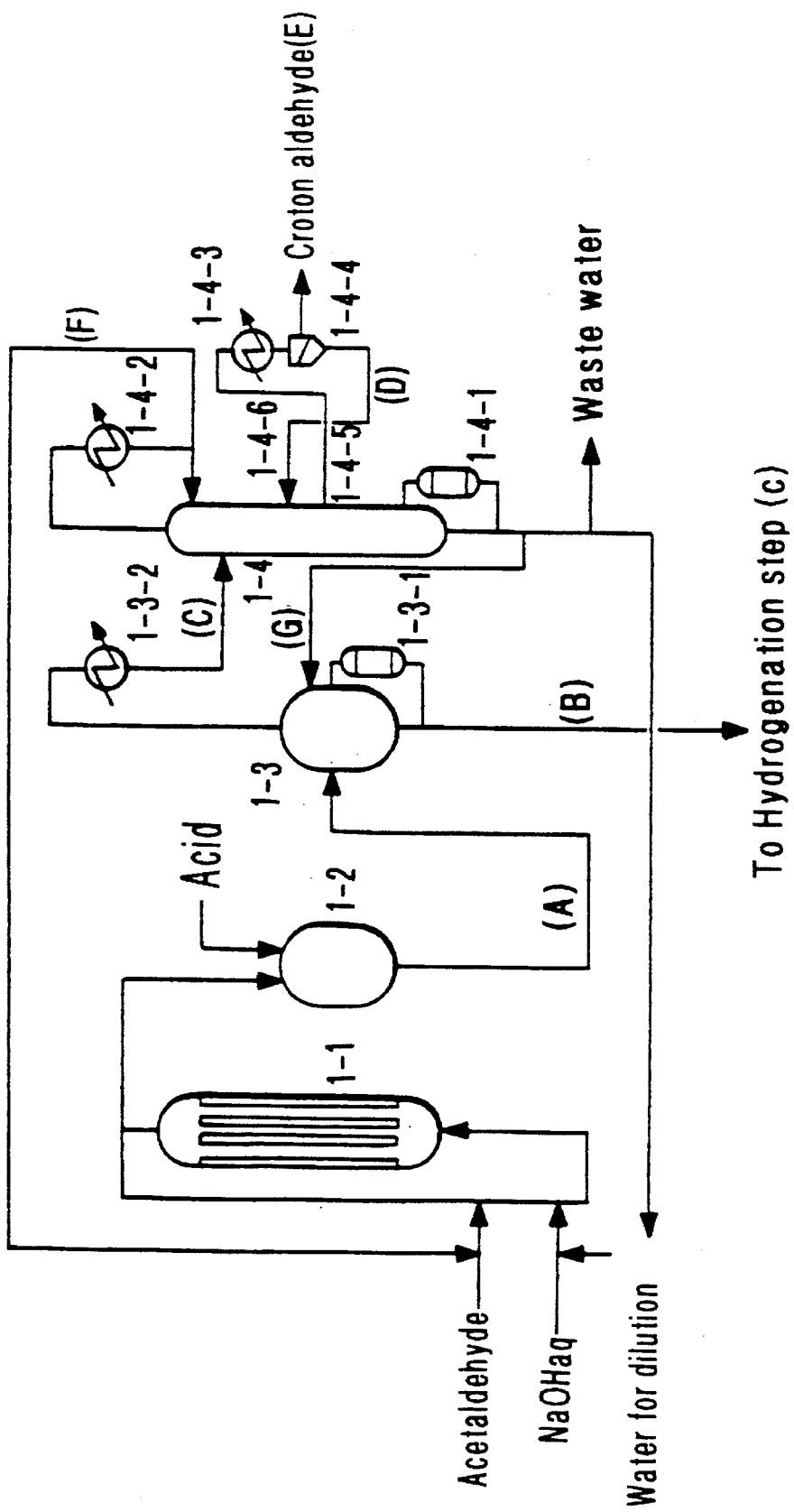
FIG. 1 is a block diagram exhibiting a process for preparing aldoxane and paraldol in which steps (a) and (b) are combinedly shown.

The crude reaction solution [stream (A) in FIG. 1] in step (a) through the first, second and third aspects is prepared by the aldol condensation of acetaldehyde in the presence of an alkali catalyst.

It is noted that the wording "not containing a substantial amount of croton aldehyde" in the first aspect of the present invention means "croton aldehyde content of less than 0.1%" based on acetaldehyde.

The crude reaction solution [stream (A) in FIG. 1] primarily contains aldoxane, unreacted acetaldehyde, water, small amounts of croton aldehyde and minor amounts of other components.

Step (a) includes an aldol condensation reactor (1-1), and supplementarily includes a neutralization tank (1-2).

Step (b) includes an aldoxane decomposition column (1-3), and supplementarily includes an acetaldehyde-refining column (1-4).

Step (c) includes a hydrogenation reactor (2-1) and supplementarily includes an alcohols distillation column (2-2), a water-distillation column (3-1), a salts removing-column (3-2), a distillation column (3-3) for removing high-boiling-points ingredients and a distillation column (3-4) for removing low-boiling-points ingredients.

And further, the aldoxane decomposition column (1-3) in step (b) supplementarily includes a reboiler (1-3-1), a condenser (1-3-2).

The acetaldehyde-refining column (1-4) supplementarily includes a reboiler (1-4-1), a condenser (1-4-2), a condenser (1-4-3) and a decanter (1-4-4) between a discharging line (1-4-5) and a recirculating line (1-4-6) which are described hereinafter.

Acetaldehyde which is a primary starting compound is charged together with an alkali catalyst such as caustic soda aqueous solution into the aldol condensation reactor (1-1) to obtain a crude reaction solution [stream (A) in FIG. 1) primarily containing aldoxane, acetaldehyde and water.

The aldol condensation reaction is usually carried out at temperatures of from 10° to 30° C.

The crude reaction solution obtained is preferably neutralized in the neutralization tank (1-2), in which the alkali catalyst is neutralized with an organic acid such as acetic acid. The use of an inorganic acid is not preferred as it causes the erosion of equipment.

The crude reaction solution [stream (A)] after the completion of neutralization is charged into the aldoxane decomposition column (1-3).

The crude reaction solution has conventionally included from 15 to 30% by weight of unreacted acetaldehyde, from 55 to 70% by weight of aldoxane, from 10 to 25% by weight of water, from 0.5 to 2% by weight of croton aldehyde and 1 to 2% by weight of various other compounds.

In the aldoxane decomposition column (1-3), aldoxane is thermally decomposed while distilling off a distillate [stream (C)] primarily containing acetaldehyde, water and croton aldehyde under ordinary pressure or reduced pressure to obtain a crude solution [stream (B)] primarily containing aldoxane, paraldol and water.

The decomposition temperatures depend upon the ordinary or reduced pressure to be applied, for example, which are generally from 60° to 120° C. from 400 to 500 Tort, and preferably 85° C. or so. The retention time is generally from 10 minutes to 2 hours, and preferably 1 hour or so, based on the charged solution.

The solution [stream (B)] discharged from the aldoxane decomposition column-bottom contains from 5 to 60% by weight of aldoxane, from 5 to 50% by weight of paraldol, from 5 to 20% by weight of water, from 1 to 3% by weight of croton aldehyde which are generated by decomposition of aldoxane and from 1 to 4% by weight of various other compounds.

The distillate [stream (C)] discharged from the top of the decomposition column (1-3) contains from 60 to 95% by weight of acetaldehyde, from 5 to 30% by weight of water, from 1 to 10% by weight of croton aldehyde which are generated by the decomposition of aldoxane and from 1 to 5% by weight of various other compounds.

Although higher decomposition temperatures and a longer retention time can preferably produce larger amounts of paraldol which is a desired compound in step (b), such undesirable compounds as croton aldehyde, etc. are also produced in larger amounts.

The solution [stream (B)] separated in step (b) as described hereinabove is supplied to a hydrogenation step (c) to prepare 1,3-butylene glycol.

In the prior art, in distilling off acetaldehyde while thermally decomposing aldoxane, water and croton aldehyde have been also distilled off together with acetaldehyde and then recirculated to the aldol condensation step (a) as it is.

This is problematic in that croton aldehyde recirculated to the aldol condensation step (a) reacts with acetaldehyde; etc., to produce various impure by-products.

Specific means in order to remove croton aldehyde from a solution [stream (F)] primarily containing acetaldehyde, water and croton aldehyde to be recirculated to the aldol condensation step (a) essentially includes a discharging line (1-4-5) from a side portion of the acetaldehyde-refining column (1-4) which also supplementarily includes a reboiler (1-4-1) and a condenser (1-4-2).

And, the discharging line (1-4-5) preferably includes a condenser (1-4-3), a decanter (1-4-4) and a recirculating line (1-4-6) to be used in an industrial process for commercial production.

A distillate discharged from the discharging line (1-4-5) is condensed in the condenser (1-4-3), and then a resulting condensate is separated into two layers of liquid in the decanter (1-4-4).

Croton aldehyde is primarily included in the upper layer of liquid [stream (E)] of the two layers of liquid, followed by supplying to a recovery step or a waste line, and resulting in being removed from acetaldehyde to be recirculated to the aldol condensation step (a).

The lower layer of liquid [stream (D)] of the two layers of liquid primarily includes from 5 to 15% by weight of croton aldehyde, and from 85 to 95% by weight of water, both of which are recirculated to the side portion of the acetaldehyde-refining column (1-4) through a recirculating line (1-4-6) in order to effectively recover croton aldehyde.

The recirculating line (1-4-6) should be situated in a portion higher than the discharging line (1-4-5) in order to decrease the acetaldehyde content in the croton aldehyde to be recovered.

A location for the discharging line (1-4-5) is selected depending upon operation conditions of the acetaldehyde-refining column (1-4).

Otherwise, the operation conditions of the acetaldehyde-refining column (1-4) are selected based on the location of the discharging line (1-4-5).

The acetaldehyde-refining column (1-4) includes a bubble-cap column, a plate column or a packed column having generally plate numbers of 20 to 30. Where the number of plates is less than 20, sufficient separation cannot be carried out, making it not preferable.

On the other hand, where the number of plates is more than 30, economical operations cannot be carried out, which is not preferable.

The discharging line (1-4-5) is located at a portion of generally 50 to 90%, preferably 70 to 80% from the top plate in the acetaldehyde-refining column (1-4).

Where the discharging line is located higher than 50%, the croton aldehyde content in the distillate at the acetaldehyde-refining column (1-4) becomes unpreferably higher.

On the other hand, where the discharging line is located lower than 10%, the croton aldehyde content in the water discharged from the bottom of the acetaldehyde-refining column (1-4) would objectionably increase.

The distillate from the discharging line (1-4-5) is generally condensed at temperatures ranging 5° to 20° C., preferably 10° to 15° C. in a condenser (1-4-3). Where the temperature is higher than 20° C., acetaldehyde is not sufficiently condensed.

It is noted that the top of the acetaldehyde-refing column (1-4) is equipped with a condenser (1-4-2), and preferably carried out in a reflux ratio of from 0.5 to 2.0.

Furthermore, the distillate from the top of the aldoxane decomposition column (1-3) must be charged into a portion above than the recirculated line (1-4-6) in the acetaldehyde-refining column (1-4) after being condensed in the condenser (1-3-2).

In accordance with a second aspect of the present invention, there is provided an improved process for the preparation of 1,3-butylene glycol by steps (a), (b) and (c);

(a) aldol condensation step of acetaldehyde in the presence of an alkali catalyst to obtain a crude reaction solution primarily containing aldoxane, acetaldehyde, water and small amounts of croton aldehyde;

(b) thermal decomposition step of aldoxane to obtain paraldol while distilling off a distillate containing acetaldehyde, water and small amounts of croton aldehyde from the crude reaction solution;

(c) hydrogenation step of paraldol to obtain 1,3-butylene glycol in the presence of a catalyst;

characterized in that water is charged into the aldoxane decomposition column in step (b).

As described in the explanation of the first aspect, the distillate [stream (C)] from the top of the aldoxane decomposition column (1-3) contains from 60 to 95% by weight of acetaldehyde, from 5 to 30% by weight of water, from 1 to 10% by weight of croton aldehyde which are generated by decomposition of aldoxane and from 1 to 5% by weight of various other compounds.

And, the removal of water would inevitably result in an increase in the viscosity of the solution [stream (B)] containing paraldol which is a desired compound discharged from the bottom of the decomposition column (1-3). In order to prevent an increase in the viscosity, water is charged into the aldoxane decomposition column (1-3), resulting in decreasing the viscosity of the solution stream (B)].

The water to be charged into the aldoxane decomposition column (1-3) may be fresh water and/or the water [stream (G)] discharged from the bottom of the acetaldehyde-refining column (1-4).

Operating temperature of the condenser (1-4-3) can be adjusted depending upon the operating pressure. Operating pressures are from 400 to 800 Torr. For examples, in the case that the operating pressure is 400 Torr, generally a temperature range from 20° to 55° C., preferably of from 30° to 40° C. is maintained.

In the case that the temperature is less than 20° C., acetaldehyde cannot be sufficiently separated and recovered.

On the other hand, in the case that the temperature is more than 55° C., water cannot be sufficiently condensed in the condenser (1-4-3).

The viscosity of the solution [stream (B)] is over approximately several hundreds centi-poise at ordinary temperatures in the case of small amounts of the recovered water [i.e. in the case of a water content of approximately 5 wt % in the stream (B)].

And further, in the case of a water content of approximately 0.1 wt % in the stream (B), it would often crystalize at ordinary temperatures, resulting in being unsuitable for practical operation.

Accordingly, the water content range in the stream (B) should be generally maintained at more than 5 wt %, preferably at more than 10 wt %, more preferably at more than 20 wt %.

For example, in the case of a water content of approximately 20 wt % in the stream (B), the viscosity of the solution [stream (B)] is approximately from 50 to 60 centi-poise at ordinary temperatures, resulting in it being suitable for practical operation without problems.

Water [stream (G)] newly charged or recirculated into the aldoxane decomposition column (1-3) in order to decrease the viscosity of the stream (B) is removed in the water distillation column (3-1) after the removal of the alcohols described below.

In accordance with a third aspect of the present invention, there is provided an improved process for the preparation of 1,3-butylene glycol by steps (a), (b) and (c);ps (a) aldol condensation step of acetaldehyde in the presence of an alkali catalyst to obtain a crude reaction solution primarily containing aldoxane, acetaldehyde, water and small amounts of croton aldehyde;

(b) thermal decomposition step of aldoxane to obtain paraldol while distilling off a distillate containing acetaldehyde, water and small amounts of croton aldehyde from the crude reaction solution;

(c) hydrogenation step of paraldol to obtain 1,3-butylene glycol in the presence of a catalyst;

characterized in that fresh water is charged into the top of a distillation column while removing water after having removed ethanol and butanol from a crude 1,3-butylene glycol solution containing ethanol and butanol obtained in said hydrogenation step (c).

A crude 1,3-butylene glycol solution obtained in the hydrogenation step (c) usually contains ethanol, butanol, water, salts generated in neutralization tank (1-2) other than 1,3-butylene glycol which is the desired product. Accordingly, ethanol and butanol have been firstly removed and then water has been removed by distillation while being partially refluxes at the top of the distillation column, followed by removing the salts, the high-boiling-point ingredients and low-boiling-point ingredients, resulting in being capable of obtaining a 1,3-butylene glycol product [e.g. described in Japanese Unexamined Patent Publication N° 156738/1988].

However, odor-causing impurities cannot be sufficiently removed only by the above-mentioned conventional water distillation, undesirably resulting in being incapable of obtaining an odorless 1,3-butylene glycol product at a high-yield.

An odorless 1,3-butylene glycol can be prepared at a high-yield through the combination of the third aspect of the present invention with the removal of the salts, the high-boiling-point ingredients and low boiling-point ingredients.

In FIG. 3, 3-1 is a water-distillation column, 3-2 is a salts-removing column (e.g. a thin-layer evaporator), 3-3 is a column for removing the high-boiling-point ingredients, 3-4 is a column for removing low-boiling-point ingredients.

A crude 1,3-butylene glycol solution after the removal of alcohols primarily containing 1,3-butylene glycol, water, the high-boiling-point ingredients, the low-boiling-point ingredients and salts is charged into the water-distillation column (3-1).

Although a perforated plate column and a bubble-cap column, etc. are to be preferably used as the water-distillation column (3-1), there can be more preferably used a packed column having low-pressure loss, in which a packing material is contained such as Sultzer-packing or Melapack (a trade name of Sumitomo Heavy Industries), etc. in order to maintain the distillation temperatures to as low as possible, which otherwise would cause the thermal decomposition of 1,3-butylene glycol above 200° C. resulting in adversely affecting it with regard to odor [described in Japanese Unexamined Patent Publication n° 156738/1988).

Furthermore, subjecting 1,3-butylene glycol to heated conditions for a long time (retention time) would also result in adversely affecting it with regard to odor.

Accordingly, preferably used is a reboiler having a short retention time in the side of process fluids, for example, a thin-layer evaporator such as a naturally falling-film type thin-layer evaporator or a force-scraping type thin-layer evaporator, etc.

The third aspect of the present invention is characterized in that fresh water is charged into the top portion of the column (3-1) while distilling off water. The fresh water may include tap water, preferably pure water (e.g. deionized water), and more preferably distilled water from the view point of an advanced refining process.

A crude 1,3-butylene glycol after removing the alcohols has to be charged into the vicinity of a middle portion of the water-distillation column (3-1). When the portion is excessively higher, the concentration of 1,3-butylene glycol in the distillate increases, unpreferably resulting in the loss of 1,3-butylene glycol.

On the other hand, when it is excessively lower, the water content in the liquid discharged from the bottom of the column (3-1) would unpreferably increase. The liquid which includes 1,3-butylene glycol containing salts and high-boiling ingredients is discharged from the bottom of the column (3-1), and then it is transferred to a salts-removing column (3-2).

The amount of the fresh water to be charged into the top portion of ,the water-distillation column (3-1) is from 1 to 200 parts by weight, preferably from 5 to 50 parts by weight based on the amount of the crude liquid to be charged.

In the case when it is less than 1 part, impurities which adversely affect the odor of a 1,3-butylene glycol product cannot be sufficiently removed. On the other hand, in the case when it is more than 100 parts, although the impurities can be sufficiently removed, the thermal energy load in the reboiler would unpreferably increase.

Reflux in the top of the water-distillation column (3-1) may be carried out or not. In the case that reflux is not carried out, the fresh water is preferably charged into the vicinity of the top of the water-distillation column (3-1).

On the other hand, in the case that reflux is carried out, the fresh water is preferably charged into the vicinity of a middle portion of the water-distillation columne (3-1).

The fresh water at room temperature can be charged without any problems.

The pressures of the top of the water-distillation column (3-1) are generally reduced pressures of less than 100 Torr, preferably 20 to 60 Torr.

In the case that the pressures are less than 20 Torr, the cooling energy load in a condenser would unpreferably increase.

When the water distillation and the charging of the fresh water are carried out at the above-mentioned pressures, the temperatures in the distillation column would be inevitably kept within a range of 20° to 40° C. at the bottom portion of the column.

As described above, compounds which are removed due to being accompanied by the newly charged fresh water primarily include butanol, 2-ethylbutanol, 2,4-dimethyl-dioxane, etc. which are produced as by-products in a hydrogenation reaction of the crude solution primarily containing aldoxane and paraldol.

As a result of the removal, the purity and yield of a 1,3-butylene glycol product are improved, resulting in effectively obtaining a high quality 1,3-butylene glycol not containing odor-causing ingredients.

In the following, although Synthesis Examples, Examples and Comparative Examples are described in order to more specifically illustrate the present invention, the scope of the present invention is not limited to the Examples.

EXAMPLES AND COMPARATIVE EXAMPLES

There were carried out aldol condensation reaction, aldoxane decomposition reaction, acetaldehyde distillation, [acetaldehyde refining (removal of croton aldehyde)], (refined) acetaldehyde recirculation to aldol condensation step, and hydrogenation reaction of a solution discharged from an aldoxane decomposition column-bottom (1-3) to prepare 1,3-butylene glycol, through steps as shown in FIG. 1.

It is noted that a water content was quantitatively measured by Karl Fisher's method, and other ingredients were quantitatively measured with a gas-chromatograph and NMR analyser.

Example 1

A 1-liter jacketed aldol condensation reactor (1-1) was charged with 500 g of acetaldehyde aqueous solution (acetaldehyde/water=88/12 by weight), after which it was cooled at temperatures ranging from 15° to 20° C.

Croton aldehyde in new acetaldehyde charged into the reactor was not detected.

Subsequently, 10 g of 0.5% caustic soda aqueous solution was gradually added dropwise as an alkali catalyst while vigorously stirring, was then allowed to react while maintaining at 20° C. for 7 hours to obtain a crude reaction solution primarily containing aldoxane, acetaldehyde, water and minor amounts of croton aldehyde.

After completion of the reaction (aldol condensation reaction) and letting it stand for 2 hours, neutralization was carried out with a diluted acetic acid in order to precisely adjust the pH to 6.2 in a neutralization vessel (1-2), followed by letting it stand for 2 hours.

Subsequently, a continuous flash evaporator [aldoxane decomposition column (1-3)] was charged with the crude reaction solution [corresponding to stream (A)] having 25.19% by weight of acetaldehyde, 61.96% by weight of aldoxane, 11.93% by weight of water, 0.45% by weight or croton aldehyde and 0.91% by weight of other ingredients after neutralization.

A distillate containing acetaldehyde, water and small amounts of croton aldehyde was distilled off from the flash evaporator in the solution temperature of 80° C. while adjusting heating temperatures for 86 minutes Coased on discharging). The relative amount of the obtained distillate [corresponding to stream (C)] was 46.5%.

There was discharged a solution [corresponding to stream (B)] having 41.44% by weight of aldoxan, 44.12% by weight of paraldol, 11.16% by weight or water 1.59% by weight of croton aldehyde and 1.68% by weight of other ingredients from the evaporator (1-3).

The distillate containing acetaldehyde, water and small amounts of croton aldehyde distilled off from the flash evaporator was charged into an acetaldehyde-refining column (1-4) equipped with a discharging line (1-4-5), a condenser (1-4-3), a decanter (1-4-4) and a recirculating line (1-4-6) while maintaining the temperature of the top of the evaporator at approximately 20° C., and that of the bottom of the evaporator at approximately 20° C., and that of the bottom of the evaporator at approximately 100° C. and ordinary pressures to obtain 192 g of a refined acetaldehyde containing croton aldehyde of less than 0.1% by removing croton aldehyde from the discharging line (1-4-5). The refined acetaldehyde was used in Example 2.

Subsequently, 200 g of the solution discharged form the evaporator bottom (1-3) was charged into a 1-liter autoclave, and then 15% by weight of a Raney nickel catalyst based on the solution was charged, followed by hydrogenation reaction in the pressure of 80 kg/cm$^2$ and the temperature of 120° C. for 30 minutes.

A crude reaction solution obtained was refined through an alcohols distillation column (2-2), a water-distillation column (3-1), a salts-removing column (3-2), a column (3-3) for removing high-boiling-point ingredients and a column (3-4) for removing low-boiling-point ingredients to obtain an odorless 1,3-butylene glycol product with a distillation yield of 76.6%, and 200. of alcohols were by-produced on 1000 of 1,3-butylene glycol. It is noted that there were conducted the odor evaluation tests in which 5 expert inspectors immediatly smelled to compare in atmosphere.

Example 2

Similar procedures as described in Example 1 were repeated, except that the refined acetaldehyde obtained in Example 1 was used by applying the operating conditions in the aldoxane decomposition column (1-3) as shown in Table 1.

The distillation yield of an odorless 1,3-butylene glycol product was 78.0%. Other results are shown in Table 1, and 280 of alcohols were by-produced based on 1000 of the 1,3-butylene glycol product.

Comparative Examples 1 and 2

Similar procedures as described in Example 1 were repeated, except that a distillate from the aldoxane decomposition column (1-3) was directly recirculated into the aldol condensation step without passing through the acetaldehyde-refining column (1-4).

The distillation yield of an odorless 1,3-butylene glycol product was 59.6% in comparative example 1 and 70.0% in comparative example 2, respectively, and 200 and 280 of alcohols were by-produced based on 1000 of the 1,3-butylene glycol product in comparative examples 1 and 2, respectively. Other results are shown in Table 1.

Operating conditions and results are shown together with the results in the Examples in Table 1.

Example 3

Similar procedures as described in Example 2 were repeated, except that temperature in the aldoxane decomposition column was changed to 85° C.

The distillation yield of an odorless 1,3-butylene glycol product was 65.0%, and 150 of alcohols were by-produced based on 1000 of the 1,3-butylene glycol product.

Comparative Example 3

Similar procedures as described in comparative example 1 were repeated, except that temperature in the aldoxane decomposition column was changed to 85° C.

The distillation yield of an odorless 1,3-butylene glycol product was 34.1%, and 1.50 of alcohols were by-produced based on 1000 of the 1,3-butylene glycol product.

TABLE 1

|  | EXAMPLE | | COMPARATIVE EXAMPLE | |
| --- | --- | --- | --- | --- |
|  | 1 | 2 | 1 | 2 |
| *Operating conditions in the aldoxane decomposition column | | | | |
| Temperature (°C.) | 80 | 75 | 80 | 75 |
| Pressure (Torr) | 760 | 760 | 760 | 760 |
| Retention time (min) | 86 | 86 | 86 | 86 |
| *Composition of a solution stream [F)] recirculated to the aldol condensation reactor (1—1) | | | | |
| Acetaldehyde/water | 88/12 | 88/12 | 87/13 | 85/15 |
| Croton aldehyde content (%) in starting acetaldehyde | <0.1 | <0.1 | 3.60 | 2.34 |
| *Composition (wt %) of a solution [stream (A)] charged into the aldoxane decomposition column | | | | |
| Acetaldehyde | 25.19 | 24.88 | 25.06 | 22.29 |
| Aldoxane | 61.96 | 63.74 | 59.76 | 65.04 |
| Paraldol | — | — | — | — |
| Water | 11.93 | 10.46 | 12.00 | 11.00 |
| Croton aldehyde | 0.45 | 0.30 | 1.61 | 0.81 |
| Other ingredients | 0.91 | 0.62 | 1.57 | 1.10 |

TABLE 1-continued

|  | EXAMPLE | | COMPARATIVE EXAMPLE | |
| --- | --- | --- | --- | --- |
|  | 1 | 2 | 1 | 2 |
| *Composition (wt %) of a crude solution [stream (B)] discharged from the aldoxane decomposition column | | | | |
| Acetaldehyde | — | — | — | — |
| Aldoxane | 41.44 | 54.50 | 38.92 | 56.71 |
| Paraldol | 44.12 | 31.25 | 43.44 | 28.39 |
| Water | 11.16 | 10.56 | 11.50 | 10.50 |
| Croton aldehyde | 0.45 | 0.30 | 2.46 | 1.70 |
| Other ingredients | 0.91 | 0.62 | 3.68 | 2.69 |
| *Composition (wt %) of a crude reaction solution after hydrogenation | | | | |
| Ethanol | 14.00 | 18.39 | 13.03 | 19.03 |
| Water | 11.42 | 10.81 | 11.76 | 10.75 |
| Butanol | 1.63 | 1.68 | 2.51 | 1.74 |
| 1,3-butylene glycol | 71.14 | 67.01 | 68.12 | 65.11 |
| High boiling point ingredients | 1.62 | 1.72 | 3.53 | 2.60 |
| Other ingredients | 0.19 | 0.39 | 1.06 | 0.77 |

Examples 4 to 7

Similar procedures as described in Examples 1 to 3 were repeated, except that an aldol condensation and an aldoxane decomposition were carried out by applying the operating conditions as shown in Table 2 in order to compare the viscosity of a solution discharged from the bottom of the aldoxane decomposition column (1-3).

Results are also shown in Table 2.

Comparative Examples 4 and 5

Similar procedures as described in Example 5 and were repeated, except that condensed water was not recirculated into the aldoxane decomposition column (1-3) by applying the operating conditions as shown in Table 2. Results are also shown in Table 2.

TABLE 2

|  | Example | | Comparative Example | | Example | |
| --- | --- | --- | --- | --- | --- | --- |
|  | 4 | 5 | 4 | 5 | 6 | 7 |
| *Operating conditions | | | | | | |
| Temperature (°C.) | 85 | 85 | 85 | 117 | 85 | 117 |
| Pressure (Torr) | 470 | 760 | 470 | 760 | 470 | 760 |
| Retention time (min) | 60 | 60 | 60 | 13 | 60 | 13 |
| *Composition (wt %) of discharged solution [stream (B)] from the bottom of the aldoxane decomposition column | | | | | | |
| Aldoxane | 13.4 | 34.8 | 26.2 | 16.0 | 21.0 | 13.5 |
| Paraldol | 63.7 | 41.7 | 72.9 | 76.2 | 58.4 | 64.2 |
| Water | 21.6 | 21.5 | 0.1 | 5.1 | 20 | 20.0 |
| Croton aldehyde | 1.3 | 2.0 | 0.8 | 2.7 | 0.6 | 2.3 |
| *Viscosity (cp/room temperature) | 62 | 50 | C | 450 | 58 | 63 |
| *Composition (wt %) of solution [stream (C)] distilled off from the top of the aldoxane decomposition column (1-3) | | | | | | |
| Acetaldehyde | 94.4 | 99.2 | 50.3 | 78.2 | 50.3 | 78.2 |
| Aldoxane | 0.7 |  | 2.4 |  | 2.4 |  |
| Croton aldehyde and others | 4.9 | 0.2 | 2.3 |  | 2.3 |  |
| Water |  | 0.6 | 45.0 | 21.8 | 45.0 | 21.8 |

Note: Viscosity value C in Comparative Example 4 indicates crystallization of the solution. The solutions discharged from the bottom of the aldoxane decomposition column in Comparative Examples 3 and 4 are high-viscosity solutions or crystallized solids compared to solutions in Examples 4, 5, 6 and 7.

Example 8

Similar procedures as described in Examples 1 to 3 were repeated, except that water distillation was carried out while charging fresh water into the top of the water distillation column (3-1).

Yield was 89% by weight based on the amount charged into the column (3-3) for removing the high-boiling-point ingredients.

Yield was 93% by weight based on the amount charged into the column (3-4) for removing the low-boiling-point ingredients.

Comparative Example 6

Similar procedures as described in Example 8 were repeated, except that water distillation was carried out without charging fresh water into the top of the water distillation column (3-1).

Yield was 83% by weight based on the amount charged into the column (3-3) for removing the high-boiling-point ingredients.

Yield was 89% by weight based on the amount charged into the column (3-4) for removing the low-boiling-point ingredients.

While the invention has been described in detail and with reference to specific embodiments thereof, it will be apparent to one skilled in the art that various changes and modifications can made therein without departing from the spirit and scope thereof.

What is claimed is:

1. A process for the preparation of 1,3-butylene glycol comprising the steps of;
   (a) aldol condensing acetaldehyde in the presence of catalyst to obtain a crude reaction solution primarily containing aldoxane, acetaldehyde, water and small amounts of croton aldehyde;
   (b) thermally decomposing aldoxane to obtain paraldol while distilling off a distillate containing acetaldehyde, water and small amounts of croton aldehyde from the crude reaction solution;
   (c) hydrogenating paraldol to obtain 1,3-butylene glycol; wherein a refined acetaldehyde not containing a substantial amount of croton aldehyde is recirculated to step (1) after removal of croton aldehyde from the distillate in step (b).

2. A process as set forth in claim 1, wherein the aldol condensation of step (a) is carried out in the presence of an alkali catalyst.

3. A process as set forth in claim 2, wherein the hydrogenation of paraldol is carried out in the presence of a catalyst.

4. A process as set forth in claim 1, wherein said removal of croton aldehyde is carried out in an acetaldehyde distillation column.

5. A process as set forth in claim 4, wherein the aldehyde distillation column has a side stream recirculating line equipped with a decanter.

6. A process for the preparation of 1,3-butylene glycol by the steps of;
   (a) aldol condensing acetaldehyde in the presence of catalyst to obtain a crude reaction solution primarily containing aldoxane, acetaldehyde, water and small amounts of croton aldehyde;
   (b) thermally decomposing aldoxane to obtain paraldol while distilling off a distillate containing acetaldehyde, water and small amounts of croton aldehyde from the crude reaction solution;
   (c) hydrogenating paraldol to obtain 1,3-butylene glycol; wherein water is charged into the aldoxane decomposition column in step (b).

7. A process as set forth in claim 6, wherein the aldol condensation of step (a) carried out in the presence of an alkali catalyst.

8. A process as set forth in claim 6, wherein the hydrogenation of paraldol is carried out in the presence of a catalyst.

9. A process as set forth in claim 6, wherein said water is water discharged from the bottom of an acetaldehyde distillation column.

10. A process as set forth in any one 6, 7 claims of 8, or 9, wherein the water to be charged into the aldoxane decomposition column is selected from fresh water and water from the bottom of the acetaldehyde refining column.

11. The process of any one of claims 6 to 9 wherein the water contents range in the stream (B) is maintained at more than 5 weight %.

12. A process for the preparation of 1,3-butylene glycol by the steps of;
    (a) aldol condensing acetaldehyde under the presence of a catalyst to obtain a crude reaction solution primarily containing aldoxane, acetaldehyde, water and small amounts of croton aldehyde;
    (b) thermally decomposing aldoxane to obtain paraldol while distilling off a distillate containing acetaldehyde, water and small amounts of croton aldehyde from the crude reaction solution;
    (c) hydrogenating paraldol to obtain 1,3-butylene glycol; wherein fresh water is charged into the top of a distillation column while removing water after having removed ethanol and butanol from a crude 1,3-butylene glycol solution containing ethanol and butanol obtained in said hydrogenation step (c).

13. The process of claim 12, wherein said fresh water is deionized water.

14. The process of claim 12 or 13, wherein said fresh water is charged in the top portion of the water-distillation column from 1 to 200 parts by weight.

15. The process of claim 6, wherein the water contents range in the stream (B) is maintained at more than 10 weight %.

16. The process of claim 6, wherein the water contents range in the stream(B) is maintained at more than 20 weight %.

17. The process of any one of claims 12 or 13, wherein said fresh water is charged in the top portion of the water-distillation column from 5 to 50 parts by weight, based on the amount of the crude liquid to be charged.

18. The process of any one of claims 12 or 13, wherein the aldol condensation of step (a) is carried out in the presence of an alkali catalyst.

19. The process of any one of claims 12 or 13, wherein the hydrogenation of paraldol is carried out in the presence of a catalyst.

* * * * *

UNITED STATES PATENT AND TRADEMARK OFFICE
CERTIFICATE OF CORRECTION

PATENT NO.   : 5,583,270
DATED        : December 10, 1996
INVENTOR(S)  : Nishiguchi It is certified that errors appear in the above-identified patent and that said Letters Patent is hereby corrected as shown below:

Title page, item [30],

"4-65186" should be -- 5-065186 --;

"4-1153856" should be -- 5-153856 --; and

"4-273829" should be -- 5-273829 --.

Signed and Sealed this

Eighth Day of April, 1997

Attest:

BRUCE LEHMAN

Attesting Officer

Commissioner of Patents and Trademarks